United States Patent
Hnat

(10) Patent No.: US 7,597,911 B2
(45) Date of Patent: Oct. 6, 2009

(54) METHOD AND COMPOSITION FOR TREATMENT OF WOUNDS AND BURNS

(75) Inventor: Thomas M. Hnat, San Diego, CA (US)

(73) Assignee: CuraPharm, Inc., San Diego, CA (US)

( * ) Notice: Subject to any disclaimer, the term of this patent is extended or adjusted under 35 U.S.C. 154(b) by 77 days.

(21) Appl. No.: 10/486,843

(22) PCT Filed: Aug. 16, 2002

(86) PCT No.: PCT/US02/26087

§ 371 (c)(1),
(2), (4) Date: Feb. 13, 2004

(87) PCT Pub. No.: WO03/015808

PCT Pub. Date: Feb. 27, 2003

(65) Prior Publication Data

US 2004/0175445 A1 Sep. 9, 2004

Related U.S. Application Data

(60) Provisional application No. 60/312,841, filed on Aug. 16, 2001.

(51) Int. Cl.
*A61K 36/736* (2006.01)
(52) U.S. Cl. .............. 424/735; 424/698; 424/740; 424/745; 424/757
(58) Field of Classification Search .............. None
See application file for complete search history.

(56) References Cited

U.S. PATENT DOCUMENTS

| 4,737,360 A | * | 4/1988 | Allen et al. | 424/60 |
| 4,915,973 A | * | 4/1990 | Costa | 424/667 |
| 5,002,760 A | * | 3/1991 | Katzev | 424/59 |
| 5,466,452 A | * | 11/1995 | Whittle | 424/750 |
| 5,942,233 A | * | 8/1999 | Chang | 424/758 |
| 6,027,728 A | | 2/2000 | Yuen | |
| 6,166,084 A | * | 12/2000 | Bloor | 514/613 |

FOREIGN PATENT DOCUMENTS

| CN | 1085784 | | 4/1994 |
| CN | 1093910 | | 10/1994 |
| CN | 1243009 A | * | 2/2000 |
| JP | 07-017845 A | * | 1/1995 |
| JP | 08283167 A | * | 10/1996 |
| JP | 10-147537 A | * | 6/1998 |
| JP | 10230069 | | 2/2000 |
| JP | 2000044481 A | * | 2/2000 |

OTHER PUBLICATIONS www.desert-tropicals.com/Plants/Rosaceae/Prunus_armeiaca.html—accessed Apr. 18, 2006.*
http://www.skinnaturalproducts.com/medicineProducts6.html—accessed Jul. 2008.*

* cited by examiner

*Primary Examiner*—Susan C Hoffman
(74) *Attorney, Agent, or Firm*—Catalyst Law Group

(57) ABSTRACT

A selection of herbal materials with curative effects combined in a liquid form and processed into a suitable topical delivery system for application to skin ulcerations, surgical incisions wounds and cuts to accomplish accelerated wound healing. The present invention can also heal and provide $1^{st}$ and $2^{nd}$ degree burn, radiation burn and sunburn relief and be used for application to human skin affected with psoriasis, eczema, dermatitis, acne, rosacea, extreme dryness, allergic reactions and inflammatory rashes. The process to manufacture and the herbal extract vehicle of delivery are both critical to the effectiveness of the present invention since the invention is comprised of two separate herbal composition extracts which do not form a homogenous mixture when combined.

3 Claims, No Drawings

METHOD AND COMPOSITION FOR TREATMENT OF WOUNDS AND BURNS

BACKGROUND OF THE INVENTION

1. Field of the Invention

The present invention relates to medicinal compositions and more particularly herbal medicinal compositions.

2. Brief Description of Prior Developments

The use of plant extracts and derivatives of plants for healing and prevention purposes has been described extensively in traditional and folk medicine literature. Over the centuries, plants have served as a major source of medicines for treating and prevention of diseases of mankind. Although recently the ability for synthesis and design of new medicines has provided new pathways for the development of therapeutic drugs, drug medicines derived from plants (phytomedicines) still have a very solid position in drugs used today. Phytomedicines are used in traditional and folk medicines by over 80 percent of the population in developing countries. In the United States, a $12 billion market has developed for plant-derived medications, some of which are part of the established medical community and some of which are part of a community referred to as folk medicine.

For centuries, extracts and derivatives of specific plants or mixtures thereof have been used for treatment of illnesses. Many of these extracts or derivatives have been documented as having clinical effectiveness in treating illnesses. Chinese medical arts rely heavily on compositions prepared and specially administered from among a relatively large selection of raw and processed herbal materials. The following are examples of such materials and applications related to human health, especially related to conditions of the skin.

The following Chinese herbal formulas are referenced from the book, *Chinese Herbal Medicine Made Easy*, Thomas Richard Joiner, Hunter House Publishers, Alameda, Calif., 2001.

See Chuang Zi Tang (Cnidium Decoction), page 350. This topical herbal formula contains among other herbs the Cnidium Fruit seed and the mineral Alum and is used to stop itching, clear infection and is useful for trichomoniasis vaginitis.

Chuan Shan Jia Qu Shi Quing Du Wan, page 39. This patent acne medicine relieves itching and reduces inflammation, sores, carbuncles, dermatitis, acne sores and hives.

Xiao Feng Tang, page 232, 310. This herbal formula contains the herbs Schizonepta, fang feng and licorice root ft cleans infection from the body and relieves skin lesions all over the body that are caused by eczema, dermatitis and psoriasis. This formula can be used topically as a soothing bath for the skin or taken internally as a decoction.

Sheng Ma Xiao Du Yin, pages 47, 48. This formula is used to treat symptoms of Aids, including Kaposi's sarcoma, and ulcerations that will not heal.

The following Chinese Herbal formula is referenced from the book, *Chinese Herb Medicine and Therapy*, Hong-yen Hsu and William G. Peacher, Keats Publishing, New Canaan, Conn., 1982.

Ching Shang Fang Feng Tang, page 96. This herbal mixture, known in China as the Siler Combination for the Skin, is a classic Chinese treatment for acne, eczema, rosacea and various skin problems. It can be taken as a tea and also used as a face tonic, applied twice a day to affected areas. This formula is made from angelica, chih-ko, cnidium, coptis, forsythia, gardenia, licorice, mentha, platycodon, schizonepeta, scute, siler, coix seeds and alum.

The present invention also comprises a selection of herbal materials with curative effects formulated and combined into an emulsion or gel for application to skin ulcerations and other skin conditions to accomplish skin regeneration and healing.

As the United States population ages, primary care physicians are likely to see increasing numbers of patients with leg ulcers. An estimated 2 million workdays are lost each year in the United States because of leg ulcers only and the medical costs of treating these nonhealing wounds can be enormous.

The prevalence of pressure ulcers (pressure sores) of the lower body in the elderly has been estimated to be between 3-11%. The morbidity and mortality associated with pressure ulcers is significant. The death rate in those patients with pressure ulcers maybe fourfold greater than in those without pressure ulcers. In addition, septic, elderly patients with pressure ulcers have a hospital mortality rate in excess of 50%. Theoretically, pressure ulcers are preventable. However, even with the best care, pressure ulcers may still occur. When they occur, treatment of pressure ulcers can be expensive. This cost includes intensive nursing care as well as adjunctive therapies such as antipressure devices, protective dressings, and skin treatments.

Leg ulcers, which usually occur below the knee, can be caused by many factors, but most are due to venous disease, arterial insufficiency, or neuropathy, alone or in combination. Diabetes is an especially important underlying condition.

Of all lower amity amputations performed annually in the United States (usually because of skin ulcers), 45% to 70% are in patients with diabetes. More than 80% of diabetic patients with foot ulcers have neuropathy, and early detection of the condition, and of angiopathy, is essential in preventing and possibly reversing the accelerated development of complications in these patients.

Some therapies for chronic leg ulcers, such as surgical debridement and split-thickness skin grafting, have been used for many years and still have a role in management. Several new methods including multiplayer compression-bandage systems, topical recombinant human platelet-derived growth factor, and human skin equivalent for use in grafting are available which may aid in wound healing however, many of these therapies are expensive and cost prohibitive for many patients.

It is an object of the present invention to provide an effective and low cost method for healing pressure ulcers and also preventing late-stage ulcer progression.

SUMMARY OF THE INVENTION

The present invention provides a composition of herbs and their extracts, which is useful to heal diabetic skin ulcerations, pressure sores, venous ulcers, surgical incisions, wounds and cuts. The combination of herbs and their extracts can accelerate the wound healing process and profoundly improve and correct other problem skin conditions.

The composition comprises *Morus albae, Artemisia argyi, Schizonepta tenuifolia, Ledebouriella seseloides, Cnidium monnieris*, alum and *Glycyrrhiza uralensis* as the "dark" extract and the *Prunus armeniaca* as the "light" extract. The material from each of the two components is an aqueous extract of the dried plant parts in a weight-to-weight ratio of about 2:1 in the final formulation.

The present invention also includes the process and methods to prepare the aqueous, herbal "light" and "dark" extracts.

The present invention contemplates topical application to the affected area of the skin in order to provide an adequate concentration of the necessary compounds in the local treatment area.

It is yet a further object of the invention to provide pharmaceutical gel and cosmetic emulsion formulations which effectively bind, stabilize and preserve the mixed "light" and "dark" herbal compositions and further act as carrier mediums to transport the active herbal components to the treatment areas.

The pharmaceutical gel and cosmetic emulsion mediums are commonly employed in medicinal and cosmetic products for controlling the consistency, physical characteristics, ease of use and the esthetic appearance of the treatment composition. Emulsifiers, natural emollients, naturally derived fatty alcohols and acids, powders, polyols, thickeners, preservatives, anti-oxidants, fragrances and other functional ingredients may be incorporated into the formulations to enhance their marketing appeal.

The methods and products of the present invention have been found to be very effective in the treatment of $1^{st}$ and $2^{nd}$ degree burns, radiation burns, sunburn and other skin conditions including psoriasis, eczema, dermatitis, acne, rosacea, extreme dryness on the body, hands and feet, allergic reactions and inflammatory rashes

DETAILED DESCRIPTION OF THE PREFERRED EMBODIMENT

In the preferred embodiment of the invention, the composition of the invention is composed of two parts one "light" and one "dark" by approximate weight percents.

Part 1: The "light" aqueous extract is composed of approximately from 9% to 11% and preferably 10% of the herb, *Prunus armeniaca*.

Part 2: The "dark" aqueous extract is composed of approximately from 2% to 4% and preferably 3% of *Artemisia argyi* from 2% to 4% and preferably 3% of *Ledebouriella seseloides*, from 2% to 4% and preferably 3% of *Schizonepta tenuifolia*, from 2% to 4% and preferably 3% of *Cnidium monnieri*, from 2% to 4% and preferably 3% of *Morus albae*, from 1% to 3% and preferably 2% of Alum, and from 0.005% to 0.015% and preferably 0.01% of *Glycyrrhiza uralensis*.

It will be appreciated by those skilled in this art that the above approximate weight percents are dependent generally on the expected potencies of the individual components, whereby the relative weight percents will vary sometimes substantially from the above individual amounts. It will be within the skilled person's knowledge with this disclosure that the objects of the present invention require the inclusion of each of the components in relative approximate weight percents above.

The availability of the herbs, the ease of manufacturing the extracts and the finished product provides an inexpensive alternative wound healing therapy, which does not have undesirable side effects. Some patients with sensitivity in the ulcer area may experience a mild burning sensation from the high concentration of electrolytes in the extracts, which on application may persist for a few minutes. A local, topical anesthetic can be used to initially decrease the skin sensitivity in the ulcer area.

Preparation of the "Light" Extract

The *Prunus armeniaca* herb is weighed then thoroughly washed in cold water to remove undesirables. Distilled or deionized water in a 10:1 dry weight ratio to the herb is then added and allowed to soak overnight. The mixture is vigorously boiled for one hour followed by a low simmer for one hour to soften the seeds. The undesirable components contained in the bitter almond meal of the *Prunus armeniaca* herb are effectively neutralized upon boiling. The aqueous mixture is then vigorously milled with high shear equipment (high shear blender or colloid mill) for approximately 30 minutes to allow the water-soluble active components to dissolve in the water medium. The unwanted insoluble material of the mixture is then removed through a step filtration process using polypropylene felt material starting at 50 microns followed by successive filtration steps at 25, 10, and 5 microns. A final polishing filtration is performed at 1 micron. The bitter almond meal filtrate that remains is a milky white color.

Preparation of the "Dark" Extract.

The *Artemisia argyi, Ledebouriella seseloides, Schizonepta tenuifolia, Cnidium monnieri* and *Morus albae* dry herbs are weighed out in equal ratios and then thoroughly washed separately in cold water. The dry weight percentages for each of these herbs are 3%. The washed botanicals are then combined. The alum herb at 2% and *Glycyrrhiza uralensis* herb at 0.01% are then weighed and added. The mixture is then steeped vigorously for one hour, and then simmered for another hour to achieve the maximum strength of the active components from each of the herbs. The "dark" extract is then filtered through a 0.45-micron paper filter.

The "light" and "dark" tracts can be standardized by replicative methods including standardization against specific compounds, which appear naturally in the extracts.

The alum is an important component bid also serves as an effective processing aid to change the dark brown color of the extract into a lighter yellowish, brown liquid. This color change is important and would otherwise prevent the formulation of an esthetically acceptable finished product.

The "dark" extract itself when added to a formulation imparts a menthol type fragrance to the mixture and can serve as the sole fragrance of the finished formulation.

The density and viscosity of the "light" and "dark" extracts are about the same as that of water.

Herbs employed in the composition of the invention in various combinations with each other and/or with other herbs can synergistically enhance the effective treatment and/or delivery through the skin.

The composition of the present invention will also contain a pharmaceutical and cosmetically acceptable carrier to bind the combined "light" and "dark" extracts into a homogenous mixture and deliver the active components of the extracts in the formulation to the desired treatment sites on the body. Amounts of the carriers for both formulations may range from about 5% to about 30%, preferably from about 10% to 20% by weight of the total composition.

In the preferred embodiment of the invention a cosmetically acceptable carrier is comprised of an oil-in-water emulsion. A pharmaceutical acceptable carrier is comprised of a water-soluble gel. Any formulation using natural based ingredients, which allows delivery of the active components of the present invention to the treatment site, is suitable for use in the present invention.

The "light" extract has a near neutral pH and the "dark" extract has an acidic pH. Both the "light" and "dark" extracts comprise a highly complex mixture of medicinally active molecules. For maximum healing effectiveness the "light" and "dark" extracts should be formulated with the carrier ingredients as soon as possible after they are manicured if they are not properly preserved.

In the cosmetic carrier emulsion a vegetable oil or other oily material should be used together with adequate emulsifiers to formulate either a water-in-oil or an oil-in-water emulsion. The concentration of specific emulsifiers depends largely on the average hydrophilic—lipopbilic balance (HLB) of the total emulsifier system employed. Because of the high electrolyte concentration in the extracts an emulsifier system incorporating both high end and low end HLB numbers is preferred.

Emulsifiers may be incorporated into the cosmetic carrier composition of the is present invention anywhere from 2% to 25%, preferably from about 3% to about 15% by weight of the total composition.

Natural emollients are incorporated into the cosmetic carrier of the present invention. Levels of such emollients may range from 3% to about 25%, preferably about 5% to 10% by weight of the total composition. Emollients may be classified under such general chemical categories as esters, fatty acids and alcohols or polyols. Naturally derived emollients are preferable and should be employed with the current invention. Suitable naturally derived fatty alcohols and acids include those compounds having from 10 to 20 carbon atoms. Especially preferred are compounds such as cetyl, myristyl, palmitic and stearyl alcohols and acids.

Among the polyols, which may serve as emollients and humectants and penetration enhancers are linear and branched chain alkyl polyhydroxyl compounds. Sorbital and vegetable glycerin are preferred because they are derived from natural components.

Another category of functional ingredients within the cosmetic composition of the present invention is thickeners. A thickener will usually be present in amounts anywhere from about 0.1% to 10% by weight, preferably from about 0.3% to 5% by weight of the composition. Natural thickeners such as xanthan, carrageenan, gelatin, karaya, alginate, guar or locust bean gums work best and are preferred. Some powdered thickeners, such as the alginate at the proper concentration, may also serve as wound exudate absorbers when applied to pressure ulcerations in the finished pharmaceutical gel formulation.

Many cosmetic compositions, especially those containing water, must be protected against the growth of potentially harmful microorganisms in addition to yeast and mold. An effective preservative system is therefore necessary. Suitable preservatives include alkyl esters of p-hydroxybenzoic acid, hydantoin derivatives, propionate salts, potassium sorbate and sodium benzoate. Preservatives will usually be employed in amounts ranging from about 0.5% to 2% by weight of the composition.

Powders may be incorporated into the cosmetic composition employed in the invention. These powders may include: oxides, chalk, talc, kaolin and smectite clays.

Other adjunct minor components may also be incorporated into the cosmetic composition. These ingredients may preferably include: natal coloring agents, opacifiers and fragrances. The effect of the preparation on the skin may also be enhanced by adding various vitamins such as vitamins A, C & B and nutrients, which also serve as antioxidants to help prevent the emollient degradation of the formulation.

Various types of additional active ingredients may also be employed in the method of the present invention. Actives are defined as skin benefit agents other than emollients and other ingredients that merely improve the physical characteristics of the composition. Although not limited to this category, general examples include: sunscreens, tanning agents, skin anti-wrinkling agents, anti-inflammatory agents, skin lighteners and moisturizers.

Final concentrations for a cosmetic, oil-in-water emulsion carrier with broad ranges in parentheses (by weight) in the resulting treatment product may include:

| | |
|---|---|
| 1) "dark" extract | 45%-55% |
| 2) "light" extract | 20%-30% |
| 3) emollients | 5%-15% |
| 4) emulsifiers | 5%-15% |
| 5) vitamins (antioxidant) | <.5% |
| 6) preservative system | 0.3%-1.0% |
| 7) fragrance | <1.0% |
| 8) thickener | <1.0% |
| | 100% by weight |

In the pharmaceutical acceptable carrier, which is a water-soluble gel, emollients, thickeners, vitamins, powders, preservatives, coloring agents, opacifiers, fragrances and other functional ingredients may be added.

The final concentration for a pharmaceutical gel carrier with broad ranges in parentheses (by weight) in the resulting treatment product may include:

| | |
|---|---|
| 1) "dark" extract (natural fragrance) | 50%-65% |
| 2) "light" extract (almond meal extract) | 25%-30% |
| 3) emollients (humectants) | 5%-10% |
| 4) vitamins (antioxidants) | <.5% |
| 5) thickeners (stabilizers) | 5%-10% |
| 6) powder (color stabilizer) | 2%-6% |
| 7) preservative system | <1.0% |
| | 100% by weight |

The study set forth below particularly illustrates the effectiveness of the invention.

Resolution of Early Stage Pressure sores. After using the Treatment Product of the Invention: A Prospective, Comparative Study.

The treatment products of the invention for the study contained either a) 50% "dark" and 25% "light" herb extracts in a cream base under the trade name Curaderm or, b) 55% "dark" and 30% "light" herb extracts in an aqueous gel base under the trade name Phytacare.

EXAMPLE 1

Introduction

During the small clinical study comparison of the healing rates of paired, early stage pressure ulcers treated with the treatment product of the invention, Eucerin, or Sween cream was evaluated. Those ulcers treated with the treatment product of the invention demonstrated a significant improvement within 14 days. The ulcers treated with either Eucerin or Sween cream had variable outcomes. Some of the ulcers were partially healed while others did not heal or progressed to a more severe state. This data suggests that the early use of specific skin creams may be useful as an adjunctive therapy in the overall treatment protocol of early stage pressure ulcers.

Resolution of pressure ulcers is dependent upon several factors: the reepithialization of the ulcer, optimization on of the nutritional status; a decrease in the shear forces on the skin. In the infirm elderly, a major factor in the formation of pressure ulcers is a decreased ability of aged skin to withstand sheer forces. Notable changes in the skin of the elderly include a decrease in the number of dermal blood vessels and alterations in the way collagen is organized and deposited. These changes may result in a decrease in the number and strength of the epidermal-derma ridges, making such skin more susceptible to injury. A reduction of local sheer forces may limit the incidence and progression of early stage pressure ulcers. The use of skin creams has been postulated to aid in the reduction of sheer forces. However, to date, there have been no clinical trials comparing the effectiveness of various skin creams for the treatment of early stage pressure ulcers. We noted previously that a specific skin cream containing the treatment product of the invention was very effective in the treatment of mild eczema (Massey P M and Malkinson F M, data not published). The elderly patients who used this skin cream also appeared to have an accelerated rate of healing of early stage pressure ulcers. We postulated that the ulcer resolution might be secondary to the lubricating effects of glycerin-based skin creams. To evaluate the efficacy of various skin creams as an adjunctive therapy for early pressure ulcers, we directly compared the healing rates of early stage pressure ulcers treated with treatment product of the invention versus matched pressure ulcers with either Eucerin or Sween cream.

Patients and Methods

This protocol was reviewed and approved by the Human Investigation Committee of the test site institution.

Ten patients with bilateral early stage ulcers were evaluated and considered for enrollment into the study. All patients were located in the geriatric medical ward of the test site institution. The requirements for enrollment included bilateral pressure ulcers at the same stage of development. The ulcers had to be at opposite but identical sides of the body (e.g. bilateral heels, bilateral hip trocanters). Only stage one and stage two ulcers were considered in this study. Stage one pressure ulcers were defined as a blanchable, erythematous patch that is warm and painful. Stage two pressure ulcers were defined as non-blanchable, erythematous and eroding into the epidermal layers. In addition, there may be a surrounding area of scaling and erythema. The excision criteria were the following: albumen less than 2.0, topical steroid, topical antibiotic, or topical emollient use in the ulcer region for at least two weeks prior. Patients were randomly assigned to one of two groups: Group A; patients treated with the treatment product of the invention and Eucerin cream, or Group B; Patients treated with the treatment product of the invention and Sween cream. Five patients used the treatment product of the invention/Sween cream combination and five patients used the Treatment product of the invention/Eucerin cream combination. The creams were applied in the following manner. The treatment product of the invention was applied to one ulcer (randomly chosen) and either. Eucerin (Group A) or Sween cream (Group B) was applied to the paired ulcer, once a day, in the morning by the ward nurses. The amount of cream applied varied per the size of the ulcer. Nurses were instructed to apply an even layer of all creams to the ulcer bed and not to vigorously rub it in. Ulcers were evaluated every other day.

The ulcer dimensions were measured at the greatest diameter and then at 90 degrees to that axis. The area was then calculated as the length times the width. The percentage area healed was calculated as follows: (original ulcer area−new ulcer area/original ulcer area)×100%. The ulcer area was measured every other day. The ulcer treatments could not be completely blinded because of the unique physical characteristics of the individual creams. The nutritional status of each patient was evaluated per the serum albumen, protein, and the cholesterol. In addition, the renal function was followed per the blood area nitrogen and creatine. The hemoglobin was also recorded.

Results

The pressure ulcers treated with Sween cream, did not demonstrate a healing rate significantly different from those treated with Eucerin cream. However, one ulcer (patient #3, stage II) treated with Sween cream did progress to a stage III ulcer and required additional medical therapy.

Discussion

This study was undertaken to evaluate the role of a specific skin cream alleged to have efficacy in the treatment of early stage pressure ulcers. We directly compared the healing rates of matched, early stage pressure ulcers treated with different skin creams (Eucerin, Sween and the treatment product of the invention). The treatment product of the invention was shown to be superior to other skin products in the treatment of early stage decubitus ulcers. This particular experiment was unique in that the creams were able to be compared "head to head" since the comparison ulcers were mirror-image locations on the same patient. Although the number of patients was small, the specific design of this study (one patient testing two creams) obviated the usual control issues found in most studies.

The patient population in this study reflected, in general, the nursing home population admitted to our hospital during the study interval. All patients were compromised and had severe underlying disease. Most were immobile and had some compromise of their mentation. These patients represent a population that is profoundly susceptible to the development and progression of pressure ulcers. In this population any therapy that prevents the breakdown of skin may impact positively on the incidence and progression of pressure ulcers. Our data suggests that the use of a specific skin cream may promote the healing of pressure ulcers. All early stage pressure ulcers treated once a day with the treatment product of the invention completely resolved within a ten-day period. The matched pressure ulcers treated with either Eucerin or Sween creams demonstrated a moderate improvement, no improvement or a progression to a later stage ulcer.

It is unlikely that the observed healing rates in the treatment product of the invention treated ulcers were due to chance alone. Although the study population was small, many variables were eliminated because the test creams were directly compared on the same patient. Patients with matched ulcers were randomized to either treatment protocols. In addition, the ulcers treated with the treatment product of the invention were randomly chosen. However, it was not possible to adequately blind the investigators as to which ulcer received which cream. The physical characteristics of each cream (odor, color, texture) were sufficiently different that the investigators could tell which ulcer was being treated with the treatment product of the invention even if the creams had been applied several hours earlier. In addition, the fragrance of the Treatment product of the invention was so distinctive, that only vigorous washing of the ulcer area would remove the odor. Vigorous washing of the ulcers was not allowed in this study (see Methods).

The use of skin creams could, theoretically, reduce the friction and sheer forces to which the skin is subjected. Sheer forces and friction have been shown to be major factors in the development and progression of pressure ulcers. Reduction of sheer forces through the use of skin creams may slow, and possibly reverse the progression of some ulcers. Until now, however, there are no controlled studies evaluating the efficacy of skin creams for the treatment of early stage pressure ulcers. Our data demonstrated that the use of a specific skin cream might make the skin suppler and less dry. This may aid in relieving some of the friction and sheer forces their skin is subjected to while in bed. A reduction in the sheer forces and friction may aid the healing of pressure ulcers. However, the treatment product of the invention treated pressure ulcers totally resolved, whereas those treated with Eucerin and Sween creams did not. Therefore, the treatment product of the invention was providing something for the healing process that the other skin creams were not It is not likely that there are major differences between the moisturizing properties of the tested creams since all three are glycerin-based. The treatment product of the invention does contain trace amounts of aloe vera (1% by weight). Aloe vera has been demonstrated to be effective in the treatment of a variety of skin disorders. However, at the concentration in the treatment product of the invention, it is unlikely that, by itself it is the reason for the dramatic differences in the healing rates of the treatment product of the invention treated ulcers. One possibility is that the fragrance may contain compounds and micronutrients that in the specific combination, significantly enhance wound healing. Although the composition of the fragrance is proprietary information, many fragrances are composed of biological extracts. Recent publications have shown that specific biological extracts can promote wound healing of damaged skin. This may be accomplished by providing micronutrients needed in the healing process, acting as a bacteriostatic agent or even stimulating the skin at the cellular level to repair itself. Regardless of the mechanism, the use of specific botanical extract to promote wound healing is very common in other cultures and is obviously present in the treatment product of the invention.

In this study we demonstrated that the use of the treatment product of the invention could be a useful adjunct in the treatment of early stage decubitus ulcers. More importantly, however, is that the regular use of the treatment product of the invention on high-risk areas may also help to prevent the formation of ulcers de novo.

The composition and method of the invention has been proven to be very effective in preventing and healing early stage pressure ulcers.

EXAMPLE 2

The composition and method of the invention have also been evaluated on a limited basis on subjects with psoriasis, eczema, acne, rosacea and xerosis. After 4-6 weeks, mild and moderate cases of psoriasis, eczema, acne and rosacea had improved or completely resolved.

Unless otherwise specially noted, all percentages herein are percentages by weight.

Thus, there have been described above various methods and products according to the present invention for treating pressure ulcers and other skin conditions. Modifications in addition to those set forth specifically above are possible within the scope of the present invention which is thus defined by the following appended claims, which are set forth as examples of the invention.

What is claimed is:

1. A medicinal composition for treating pressure sore ulcerations comprising aqueous extracts consisting of an effective amount of *Prunus armeniaca*, approximately 2% to 4% by weight of *Artemisia argyi*, 2% to 4% by weight of *Ledebouriella seseloides*, 2% to 4% by weight of *Schizonepeta tenuifolia*, 2% to 4% by weight of *Cnidium monnieri*, 2% to 4% by weight of *Morus albae*, 1% to 3% Alum, and 0.005% to 0.015% by weight of *Glycyrrhiza uralensis*.

2. The composition according to claim 1 wherein the composition is a gel.

3. The composition according to claim 1 wherein the composition is an oil-in-water emulsion.

* * * * *